US007731984B2

(12) United States Patent
Sztejnberg et al.

(10) Patent No.: US 7,731,984 B2
(45) Date of Patent: Jun. 8, 2010

(54) SPECIES OF FUNGI AND THEIR USE IN PEST AND DISEASE CONTROL

(75) Inventors: Abraham Sztejnberg, Rehovot (IL); Uri Gerson, Rehovot (IL); Aviva Gafni, Rishon LeZion (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 913 days.

(21) Appl. No.: 10/502,486

(22) PCT Filed: Jan. 23, 2003

(86) PCT No.: PCT/IL03/00059

§ 371 (c)(1),
(2), (4) Date: Feb. 10, 2005

(87) PCT Pub. No.: WO03/062403

PCT Pub. Date: Jul. 31, 2003

(65) Prior Publication Data

US 2005/0119125 A1      Jun. 2, 2005

(30) Foreign Application Priority Data

Jan. 24, 2002    (IL)    ..................... 147835

(51) Int. Cl.
*A61K 36/06*   (2006.01)
*A61K 36/09*   (2006.01)
*A01N 25/00*   (2006.01)
*A01N 63/04*   (2006.01)
*A01N 65/00*   (2006.01)

(52) U.S. Cl. ................. 424/405; 424/93.5; 424/195.15; 435/254.1; 435/911

(58) Field of Classification Search ........................ None
See application file for complete search history.

(56) References Cited

FOREIGN PATENT DOCUMENTS

EP            0353662 B1         4/1994

OTHER PUBLICATIONS

Agrios, G.N. (1997) *Plant Pathology*, 4th ed. (Academic Press; New York), pp. vii-xv and 619-635.
Argov, Y. et al. (2002) "Rearing, Release and Establishment of Imported Predatory Mites to Control Citrus Rust Mite in Israel", *BioControl* 47: 399-409.
Avis, T.J. et al. (2001) "Specificity and Mode of Action of the Antifungal Fatty Acid cis-9-Heptadecenoic Acid Produced by *Pseudozyma flocculosa*", *Applied and Enviromental Microbiology* 67: 956-960.
Boekhout, T. et al. (Feb. 28, 2003—published online) "New Anamorphic Mite-Associated Fungi Belonging to the Ustilaginomycetes: *Meira geulakonigii* gen. et sp. nov., *Meira argovae* sp. nov. and *Acaromyces ingoldii* gen. nov. et sp. nov.", *IJSEM* 53: 1655-1664.
Copping, L.G. (ed.) (1998) *The BioPesticide Manual*, 1st ed. (British Crop Protection Council; Farnham, UK), table of contents.
Golubev, W. et al. (1998) "Killer Activity of *Tilletiopsis albescens* Gokhale: Taxonomic and Phylogenetic Implication", *Systematic and Applied Microbiology* 21: 492-432.
Helle, W. & Sabelis, M.W. (eds.) (1985) "Spider Mites, Their Biology, Natural Enemies and Control", *World Crop Pests* (Elsevier; Amsterdam), vol. 1A and 1B: prefaces, table of contents and indexes.
Hijwegen, T. (1986) "Biological Control of Cucumber Powdery Mildew by *Tilletiopsis* minor", *Netherlands Journal of Plant Pathology* 92: 93-95.
Horsfall, J.G. & Barratt, R.W. (1945) "An Improved Grading System for Measuring Plant Diseases", *Phytopathology* 35: 655.
Lindquist, E.E. et al. (eds.) (1996) "Eriophyoid Mites, Their Biology, Natural Enemies and Control", *World Crop Pests* (Elsevier; Amsterdam), vol. 6: preface, table of contents and index.
Palevsky, E. et al. (2000) "Mite Problems On Citrus and Control Strategies in Israel", *Proceedings of the International Congress of Citriculture*, IX Congress: 760-763; and.

(Continued)

*Primary Examiner*—David M. Naff
*Assistant Examiner*—Debbie K Ware
(74) *Attorney, Agent, or Firm*—John P. White; Cooper & Dunham LLP (57) ABSTRACT

The present invention describes substantially pure cultures of three new species of fungi, *Meira geulakonigae* (CBS 110052), *Meira argovae* (CBS 110053) and *Acaromyces ingoldii* (CBS 110050) (all nom. prov.), wherein said cultures are biologically pure. The conditioned medium for all three new fungi species is also described, as well as their biologically active products. The biological product of the three new fungi species and their conditioned medium has miticidal and fungicidal activities. Thus, a composition for the control of mites and/or phytopathogenic fungi comprising a biocontrol agent derived from any one of the three new fungi species is also described, optionally comprising an agriculturally compatible carrier. Finally, the present invention describes a method for producing a fungicide and/or a miticide, wherein the active ingredient of said fungicide/miticide is any one of *M. geulakonigae*, *M. argovae*, or *A. ingoldii*, or any combination thereof, and/or a culture thereof, and/or any product or derivative thereof, comprising culturing said fungus and optionally isolating said active ingredient from the culture.

10 Claims, 8 Drawing Sheets

OTHER PUBLICATIONS

Sztejnberg, A. et al. (1989) "*Ampelomyces quisqualis* for Biological and Integrated Control of Powdery Mildews in Israel", *J. Phytopathology* 124: 285-295.

Official Action issued Mar. 23, 2007 in connection with European Patent Application No. 03 706 867.3.

van der Geest, L.P., et al. Diseases of mites. Exp Appl Acarol. Jul. 2000;24(7):497-560.

Avis, T.J., et al. Molecular and Physiological Analysis of the Powdery Mildew Antagonist *Pseudozyma flocculosa* and Related Fungi. Phytopathology. Mar. 2001;91(3):249-54.

Paz, Z., et al. Assaying Three New Fungi Against Citrus Mites in the Laboratory, and a Field Trial. BioControl. Dec. 2007;52(6):855-862.

Braun, U. *A monograph of the Erysiphales (powdery mildews)*. Berlin-Stuttgart: Beih. Nova Hedwigia 89, 1987. pp. 1-5 and 33-35.

Official Action issued Sep. 21, 2009 in connection with Canadian Application No. 2,473,957.

SPECIES OF FUNGI AND THEIR USE IN PEST AND DISEASE CONTROL

This application is a §371 U.S. national stage application of PCT International Application No. PCT/IL03/00059, filed Jan. 23, 2003, claiming priority of Israeli Application No. 147835 filed Jan. 24, 2002, the contents of all of which are hereby incorporated herein by reference.

FIELD OF THE INVENTION

The present invention relates to three new species of fungi of the Subdivision Basidiomycotina, Order Ustilaginales, to any products or other chemicals obtained therefrom or from their progeny and/or any mutants thereof, and to their use in the control of pests, particularly pestiferous mites (Acari) and pathogenic plant fungi, especially powdery mildews.

BACKGROUND OF THE INVENTION

Plant diseases caused by fungi and mites have a significant adverse impact on the production of important crops worldwide.

Pest mites belong to two main families. The most important family is Tetranychidae, also known as the spider mites. These mites cause widespread damage to almonds, apple, avocado, cassava, citrus, cotton, grapes, tea, various greenhouse crops like cucumber, pepper and tomato, and several ornamentals, including roses and chrysanthemums [Helle, W. & Sabelis, M. W. *Spider Mites, Their Biology, Natural Enemies and Control*, Volumes. I and II, Elsevier, Amsterdam (1985)]. The other family, Eriophyidae, corresponds to the rust or gall mites, which can be major pests of apple, citrus, coconut, pear, currants and berries, as well as many vegetables and ornamentals [Lindquist et al. (Eds.) *Eriophyoid Mites, Their Biology, Natural Enemies and Control*. Elsevier, Amsterdam (1996)]. The carmine spider mite, *Tetranychus cinnabarinus*, and the citrus red mite, *Panonychus citri*, belong to the former family, whereas the citrus rust mite, *Phyllocoptruta oleivora*, to the latter. In Israel, the carmine spider mite is an important pest of vegetables and ornamentals, whose chemical control has met increasing difficulties due to evolving resistance to pesticides. The citrus red mite is of minor importance, whereas the citrus rust mite is the major pest of citrus in Israel and many other parts of the world. Local citrus growers have been encountering serious problems in the chemical control of the citrus rust mite, due to its increased resistance to acaricides and the presence of pesticide residues on exported fruit [Palevsky et al. Mite problems on citrus and control strategies in Israel. *Proceedings of the International Congress of Citriculture*, (in press)]. In counterpart, biological control of this pest with introduced predators has just begun and is still uncertain [Argov, Y., S. Amitai, G. A. C. Beattie and U. Gerson. Rearing, release and establishment of imported predatory mites to control citrus rust mite in Israel. *BioControl*, 47: 399-409 (2002)].

Likewise, fungal phytopathogens cause major and severe economic losses in the agricultural and horticultural industries. Germination and growth of infected plants are inhibited; plants succumb to soft rot and may even die. Infested soils are unsuitable for growing certain crops. The powdery mildews are the most common, widespread and easily recognizable plant diseases. They are caused by fungi of the family Erysiphaceae, which are grouped into seven main genera [Agrios, G. N. *Plant Pathology*, 4th ed. Academic Press, New York (1997); Braun, U. *A Monograph of the Erysiphales (Powdery Mildews)*, J. Cramer, Grebruder Borentraeger, Berlin (1987)]. Powdery mildews are characterized by spots or patches of a white to grayish powdery growth on young plant tissues, which can cover entire leaves and other organs of the plant [Agrios (1997) id ibid.]. Powdery mildews are very often present on crop plants and ornamentals, and the yield losses that they incur annually on all crops probably surpasses the losses caused by any other single type of plant disease. Crops that suffer severely from powdery mildews include wheat, barley, cucumber, squash, strawberry, grape, apple, mango, ornamentals such as rose, begonia, lilac and many others [Agrios (1997) id ibid.]. Chemical fungicides usually control these diseases, but this mode of control is continuously being challenged by the rapid development of resistance to the recommended fungicides. As for the mites pest, biological control of fungal phytopathogens is just in its infancy as well. Although the biofungicide AQ10 has been registered for powdery mildews control since 1996, the extent of its use is still moderate when compared to the use of chemical fungicides [Copping, L. G. (Ed.) *The BioPesticide Manual*, 1$^{st}$ ed. British Crop Protection Council, Farnham (1998); Sztejnberg et al. *Ampelomyces quisqualis* for biological and integrated control of powdery mildews in Israel. *J. Phytopathology* 124:285-295 (1989)]. Overall, world expenditure for fungicides to control powdery mildews is estimated to be circa one billion US dollars per year.

In summary, plant mites and fungal phytopathogens are still mostly controlled with chemical acaricides and fungicides, despite the above-mentioned corollary problems. Thus, the widespread abuse of pesticides and the emergence of pest resistance to most of these chemicals has increased the demand for environmentally-friendly biological pesticides, or "biopesticides" [Copping, 1998, id ibid.].

In order to fulfill this demand, it is a major object of the invention to provide new species of fungi that possess activity against plant mites and fungi, and that can be used against them. Another object of the invention is to provide anti-fungal and anti-miticidal preparations, or biopesticides.

So far, there has been no indication that any of the three new fungal species hereby described and claimed, have had any adverse effect on the plants with which they were in contact in any way, nor were they detrimental to any other organism (except the pests being assayed against). It is therefore a further object of the invention to provide miticidal and fungicidal compositions that would be devoid of adverse effects on the treated plants, or on the environment.

These and other objects of the present invention will become apparent as the description proceeds.

SUMMARY OF THE INVENTION

The present invention relates to three new species of fungi of the Subdivision Basidiomycotina, Order Ustilaginales, and to their use in the control of pests, particularly pestiferous mites (Acari) and pathogenic plant fungi, especially powdery mildews.

As presently claimed, the present invention relates to a substantially pure culture of the fungus *Meira geulakonigae* nom. prov. (*M. geulakonigae*), a substantially pure culture of the fungus *Meira argovae* nom. prov. (*M. argovae*), and a substantially pure culture of the fungus *Acaromyces ingoldii* nom. prov. (*A. ingoldii*), as well as their respective conditioned media.

All of the fungi cultures of the invention are biologically pure.

The three new fungi species have been deposited in the Centraal Bureau voor Schimmelcultures (CBS), Institute of the Royal Netherlands Academy of Arts and Science, under the provisions of the Budapest Treaty for the Deposit of Microorganisms.

The present invention also relates to biologically active products derived from fungi selected from the group consisting of *M. geulakonigae, M. argovae* and *A. ingoldii*, wherein said biological activity is miticidal and/or fungicidal.

The present invention provides a composition for the control of mites and a composition for the control of fungi. Both compositions comprise a biocontrol agent derived from any or at least one of the fungi of the invention, and/or from a product thereof. The biocontrol agent consists of spores and/or products thereof. The miticide and the fungicide composition may further comprise an agriculturally compatible carrier, extracted from a liquid culture of the respective fungi. In this respect, said carrier may be selected from the group consisting of water, culture medium, oils or any other adjuvants or carriers.

The miticide composition of the invention is available in the form of a liquid suspension containing about between $10^7$ to $10^{10}$ spores/ml, preferably about $10^9$ spores/ml.

The fungicide composition of the invention is available in the form of liquid suspension containing between about $10^7$ to about $10^{10}$ spores/ml, preferably about $10^8$ spores/ml.

Both miticide and fungicide compositions of the invention may further comprise a conventional adjuvant used in formulations for biocontrol agents.

It is another aspect of the present invention to provide a method for producing a fungicide and/or a miticide, wherein the active ingredient of said fungicide/miticide is any one of *M. geulakonigae, M. argovae*, or *A. ingoldii*, or any combination thereof, and/or a culture thereof, and/or any product or derivative thereof. This process comprises culturing a fungus of the invention, and optionally isolating said active ingredient from the culture.

In a particular embodiment, the method comprises the steps of: (a) cultivating, under aerobic or anaerobic conditions, any one of the fungi of the invention in an appropriate culture medium, (b) harvesting the culture; (c) separating the spores from the liquid medium; and either (d) suspending the spores in an agriculturally compatible liquid carrier to give a fungicide/miticide in liquid form; or (e) lyophilizing the spores, to give a dry form fungicide/miticide. Said dry form fungicide/miticide can be further dissolved in an agriculturally compatible liquid carrier. In this method, the fungus is to be cultured at a temperature of from about 20° C. to about 30° C., preferably from about 23° C. to about 27° C., and more preferably at about 25° C. The pH of the fungi culture should be from about 5.1 to about 5.6, preferably a pH of 5.1 is ideal.

Lastly, the invention provides a method for controlling mite and/or fungi infestations in plants susceptible thereto, which comprises applying to the plant the miticide or the fungicide composition of the invention. The mite infestation may be caused by *Phyllocoptruta oleivora* (citrus rust mite) or other rust and gall mites, by *Tetranychus cinnabarinus* (carmine spider mite), and/or *Panonychus citri* (citrus red mite) or other spider mites, while the fungal infestation is usually due to *Sphaerotheca fusca* (powdery mildew) or other powdery mildews. Any commercial plants susceptible to spider mites, rust mites, gall mites or to phytopathogenic fungal diseases, in particular to powdery mildew, may be treated with the miticide and/or with the fungicide composition of the invention.

All the above and other characteristics and advantages of the invention will be further understood through the following illustrative and non-limitative description of preferred embodiments thereof, with reference to the appended figures.

BRIEF DESCRIPTION OF THE FIGURES

AS001 represents *Acaromyces ingoldii* nom. prov.; AS004 represents *Meira geulakonigae* nom. prov.; and AS005 represents *Meira argovae* nom. prov.

Graph showing the coverage of cucumber leaves (in percentage) by powdery mildew (PM) before or after infection, and treated or untreated with *M. geulakonigae*. Different treatments are represented as: W, no infection, water only; Mg, no infection, *M. geulakonigae* only; PM-W, infection first, then water; PM-Mg, infection first, then *M. geulakonigae*; W-PM, water first, then infection; Mg-PM, *M. geulakonigae* first, then infection. A, B, C and D denote 13, 20, 27 and 53 days post-treatment, respectively. Abbreviations: L. cov., leaf coverage.

Graph showing the average cucumber yield in weight (g) of plants infected with powdery mildew, before or after treatment with a suspension of *M. geulakonigae* spores. Different treatments are represented by the abbreviations as in FIG. 3. Abbreviations: Wt., weight.

FIG. 5A-B: *Meira geulakonigae* nom. prov. reduces foliage mortality and increases the yield of cucumber plants.

FIG. 6A-B: *Meira geulakonigae* nom. prov. reduces the covering of cucumber plants by powdery mildew (*Sphaerotheca fusca*).

FIG. 6B: Close-up of (A). Right: natural infection of PM on cucumber plants. Left: natural infection of PM on cucumber plants that were treated with *M. geulakonigae*.

Abbreviations: Mg, *M. geulakonigae*; n.-tr., non-treated; tr., treated.

Graph showing the number of leaves infested by at least one carmine spider mite on cucumber leaves treated with *M. geulakonigae*. Data collected from three examinations over a period of 16 days, in a pilot commercial greenhouse. Different treatments are represented by the abbreviations as in FIG. 3. Abbreviations: No. L., number of leaves.

Graph showing the percent mortality of citrus rust mite on citrus leaves, after treatment with *M. geulakonigae* ($10^9$ spores/ml).

Abbreviations: T, treated; C, control; Mort., mortality.

DETAILED DESCRIPTION OF THE INVENTION

The subject of the present invention concerns the use of biocontrol agents of fungal origin to control certain pests. Specifically exemplified herein is the use of the novel species of the invention, *Meira geulakonigae* nom. prov. (*M. geulakonigae*), *Meira argovae* nom. prov. (*M. argovae*) and *Acaromyces ingoldii* nom. prov. (*A. ingoldii*).

Note 1: The finding of the species subject of this patent application was not published at the time of submitting this application. Therefore, for the purposes of the art of Taxonomy the names of the respective species are considered provisional, and require the notation "nom, prov." Since the application was filed these names have become the recognized names of the fungi, as appears in Boekhout, T., et al., International Journal of Systemic and Evolutionary Microbiology (2003), 53, 1655-1664. The deposit numbers in Boekhout et al are those appearing in the Table on page 10 hereinafter.

Note 2: For the purposes of this patent application, *Meira geulakonigae* nom. prov. is equivalent to *Meira geulakonigii* nom. prov.

A further aspect of the subject invention includes compositions and formulations which are highly effective in delivering the biocontrol agent to the target pest and are apparently devoid of any adverse effects on the treated plants and/or the environment.

Substantially pure cultures of *A. ingoldii*, *M. geulakonigae* and *M. argovae* (all nom. prov.) have been deposited in the Centraal Bureau voor Schimmelcultures (CBS), Institute of the Royal Netherlands Academy of Arts and Science (P.O. Box 85167, 3508 AD, Utrecht, The Netherlands), as follows:

| Culture | Patent restricted No. | Deposit Date | Accession No. |
|---|---|---|---|
| *Acaromyces ingoldii* nom. prov. L1/AS001 | CBS 109901 | Dec. 12, 2001 | CBS 110050 |
| *Meira geulakonigae* nom. prov. L4/AS004 | CBS 109902 | Dec. 12, 2001 | CBS 110052 |
| *Meira argovae* nom. prov. L5/AS005 | CBS 109903 | Dec. 12, 2001 | CBS 110053 |

The deposits are available as required by foreign patent laws in countries wherein counterparts of the subject application, or its progeny, are filed. However, it should be understood that the availability of the deposits does not constitute a license to practice the subject invention in derogation of patent rights granted by a governmental action.

Further, the subject culture deposits were stored and made available to the public in accord with the provisions of the Budapest Treaty for the Deposit of Microorganisms, i.e., they were stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

It is to be understood, that a substantially pure culture is a culture that may comprise variations which a person of ordinary skill in the art would know would not defeat the stated purpose of the invention, and which would still be within the present inventive concept.

Preferred cultures, according to the invention, are biologically pure cultures. By "biologically pure", as used herein, is meant a culture free of deleterious viable contaminating microorganisms.

Two of new fungal species of the invention, namely *M. geulakonigae*, and *A. ingoldii* (all nom. prov.), were obtained from cadavers of the citrus rust mite, found on citrus leaves in two ecosystems in Israel, specifically the Upper Galilee region and the south of the Coastal Plain. The third new fungal species, *M. argovae* (nom. prov.), was isolated from the cadaver of the carmine spider mite found on the leaf of a castor bean (*Ricinus communis*) bush, in Ness Ziona, in the central Coastal Plain of Israel.

Figure 1:
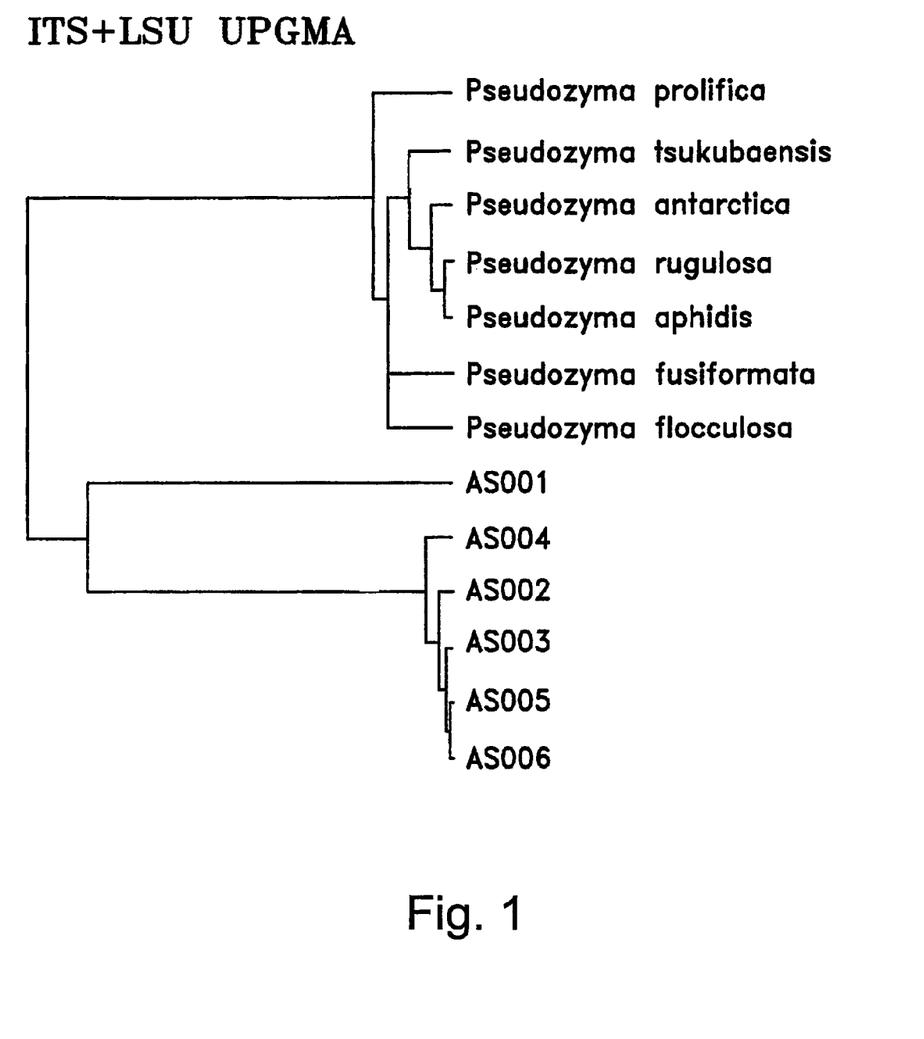
FIG. 1: Dendrogram showing the taxonomic classification of the three fungal species.

Taxonomic, morphological and molecular characterizations were made using the methods recommended by the CBS. It is to be mentioned that due to their minute size, all of the novel species could only be characterized by molecular biology techniques. The three species are within the Subdivision Basidiomycotina, Order Ustiginales. The dendrogram shown (FIG. 1) is a representation of the outcome of a phylogenetic analysis of a molecular study for the correct placement of the fungi, indicating the clear separation of the three new species. Along the dendrogram, the three new species are denoted as: *Acaromyces ingoldii* nom. prov., AS001; *Meira geulakonigae* nom. prov., AS004; and *Meira argovae* nom. prov., AS005. More precise determinations were done with the Internal Transcribed Spacer of Large Sub Units (ITS-LSU), and run on the Unweighted Pair-Group Method using Arithmetic Averages program (UPGMA), and the LSU-ITS Principal Component Analysis (PCA) methods. The resulting drawings demonstrate the unambiguous positioning of the three new species (FIG. 1 and data not shown).

Figure 2:
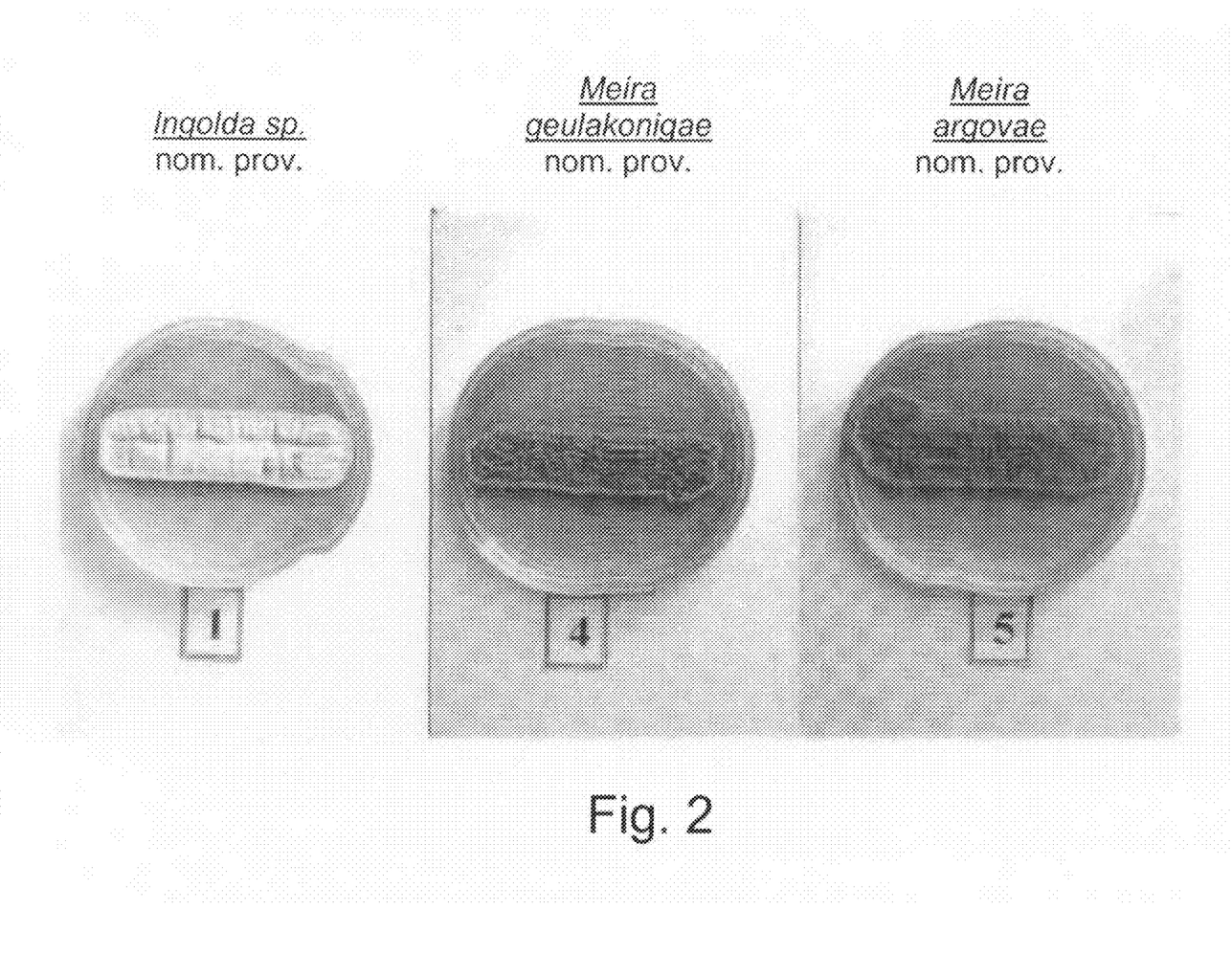
FIG. 2: Photographs of the three new fungal species.

Photographs of the three fungi species are presented in FIG. 2. The three species were grown on potato dextrose agar (PDA) for 11 days at about 25° C. FIG. 2a shows *A. ingoldii*, whose colony is whitish, whereas *M. geulakonigae* (FIG. 2b) and *M. argovae* (FIG. 2c) are brownish. Both *M. geulakonigae* and *M. argovae* colonies secrete pigments into the media, and *M. argovae* secrets higher quantities. The three species demonstrated differences in colony growth pattern. *M. geulakonigae* colony is more woolish, whereas *M. argovae* shows an almost segmented growth pattern. Fungal growth was similar under light and dark conditions. None of the three species has shown any chitinolytic or proteolytic activities.

Thus, in a first aspect, the invention provides substantially pure cultures of each of the fungi *M. geulakonigae*, *M. argovae* and *A. ingoldii* (all nom. prov.). Specifically, the invention provides substantially pure cultures of the fungi deposited at the CBS under Accession Nos. CBS 110052, CBS 110053 and CBS 110050.

It is known in the art how to obtain mutants of microorganisms without altering the characteristics thereof. For instance, mutants may be obtained by treatment with physical or chemical mutagens, such as UV light, X-rays, gamma-rays and chemicals such as n-methyl-N'-nitro-N-nitrosoguanidine. It is also known in the art how to obtain natural variants, e.g. by screening cultures of the parental strain. Therefore, the invention also pertains to the mutants or variants of *M. geulakonigae*, *M. argovae* and *A. ingoldii* (all nom. prov.) which retain the characteristics described herein, particularly mutants of the fungi deposited at the CBS under Accession Nos. CBS 110052, CBS 110053 and CBS 110050.

In one embodiment, the fungi of the invention may be cultured by any methods known in the art for their culture, e.g. anaerobic cultivation, aerobic cultivation on agars, or submerged aerobic fermentation in fermentors. Preferably, the culture is fermented submerged.

The media for growth or fermentation may contain assimilatable carbon sources and digestible nitrogen sources. Suitable carbon sources include, but are not limited to, glucose, lactose, mannitol, dextrin, corn, starch, xylose, fructose, lactose and the like.

Suitable nitrogen sources include, but are not limited to, natural nitrogen-containing materials and the products thereof, e.g. meat extracts, peptones, corn infiltration solutions, yeast extracts, soy bean meals, tryptones, cotton seed meals, wheat meals, and the like. Organic or inorganic nitrogen-containing materials may also be used, e.g. urea, nitrates and ammonium salts, such as sodium nitrate, ammonium acetate, ammonium chloride, ammonium sulfate, ammonium phosphate, and the like.

Optionally, the media for cultivating M. geulakonigae, M. argovae and A. ingoldii (all nom. prov.) may also contain inorganic salts, trace elements, and growth stimulators.

The inorganic salts suitable for use in the media for cultivating M. geulakonigae, M. argovae and A. ingoldii (all nom. prov.) include, but are not limited to, salts capable of yielding zinc, sodium, magnesium, calcium, ammonium, chloride, carbonate, sulfate nitrate, and the like.

In addition, essential trace elements necessary for the growth and development of the organisms may also be included in the culture media. Such trace elements commonly occur as impurities in other components of the media in an amount sufficient to meet the growth requirements of the organism.

The growth stimulators suitable for use in the invention include, but are not limited to, glycerol and sodium salts, such as sodium acetate, sodium glutamate, sodium tartarate, and the like.

The fungi of the invention should be grown at temperatures of from about 20° C. to about 30° C., preferably from about 23° C. to about 27° C., more preferably at about 25° C.

As is customary in aerobic culture processes, sterile air is blown into the vessel from the bottom while the medium is stirred with conventional turbine impellers. In general, the aeration rate and agitation rate should be sufficient to maintain a level of dissolved oxygen of at least 30% of air saturation with an internal vessel pressure of 0.2 bars.

The pH value in the fermentator varies along with the culture media and the quantity of inocula used. Typically, the pH value is maintained weakly acidic. If necessary, prior to inoculation or during the fermentation, the pH value in the fermentator can be appropriately adjusted to be weakly acidic e.g. about pH 5.1±0.2 to about pH 5.6. Preferably, the pH value prior to inoculation is adjusted to about pH 5.1.

Any basic materials known in the art can be used to adjust the pH value, e.g. alkaline metal salts, such as sodium salts, and the like.

In principle, the time for cultivating M. geulakonigae, M. argovae or A. ingoldii (all nom. prov.) should be enough to produce a sufficient amount of spores. In general, the cultivation is conducted for about 5 to about 8 days at the said temperatures, preferably at 25° C.

Furthermore, anti-foam agents can be appropriately added during the fermentation to inhibit excessive foam formation. For instance, polypropylene glycol of a molecular weight of about 2000 can be added to the culture medium at an amount of about 0.2 g/liter of culture medium.

The term "conditioned medium" used in the specification refers to the whole contents in a flask or fermentor, including both the cellular and non-cellular components, resulting directly from the fermentation of any or a combination of the fungi of the invention in an appropriate culture medium without being subject to filtration, separation or purification.

Thus, the conditioned medium of any one of the fungi of the invention is obtained upon cultivating the said fungi in the above-specified culture medium and under the above-specified pH, temperature and duration.

Example 1 shows the activity of M. geulakonigae, M. argovae and A. ingoldii in the control of powdery mildew in the cucumber plant, while in Examples 2 and 3, the three new fungi species are used in the control of pest mites. Similarly, the conditioned medium of the fungi of the invention shall be active in the control of pest mites, such as the carmine spider mite (Tetranychus cinnabarinus) the citrus red mite (Panonychus citri), the oriental red mite, (Eutetranychus orientalis) and the citrus rust mite (Phyllocoptruta oleivora), and phytopathogenic fungi. The active ingredient in the conditioned medium is any compound that is toxic and/or incompatible with the life or growth of pest mites and/or phytopathogenic fungi.

The conditioned medium can be used directly for the control of pest mites and phytopathogenic fungi or as part of a composition of the invention, as described below.

In another aspect, the invention relates to a composition or formulation for the control of pests, comprising as effective ingredient any one of the fungi M. geulakonigae, M. argovae or A. ingoldii (all nom. prov.), or any effective biocontrol agent derived from said fungi, or progeny or mutants thereof or from a culture medium used for growing the same, any product or any mixture thereof.

In a preferred embodiment, the biocontrol agent is derived from the group consisting of spores and conidia, preferably spores and/or products thereof.

Any one of the fungi of the invention, M. geulakonigae, M. argovae or A. ingoldii (all nom. prov.), may produce or contain a compound, which may be a nucleotide, a protein, traces of metals, that are, directly or indirectly, toxic or incompatible with the life of pest mites and/or phytopathogenic fungi. These are herein referred as products thereof, or more specifically biologically active products thereof. Similarly, the products may also be derived from the group consisting of spores and conidia, preferably spores, derived from the fungi of the invention.

In Examples 2 and 3, mite-infested cucumber and citrus seedlings plants are treated with M. geulakonigae and the level of infestation significantly decreases when compared with water-treated or untreated infested plants. Thus, in one embodiment, the composition of the subject invention is intended for the control of plant-infecting mites (Acari). In a preferred embodiment, the pest mites are the carmine spider mite (Tetranychus cinnabarinus) the citrus red mite (Panonychus citri), the oriental red mite, (Eutetranychus orientalis) and the citrus rust mite (Phyllocoptruta oleivora).

The composition for the control of mites comprises an aqueous suspension, containing between about $10^7$ to $10^{10}$ spores/ml, preferably $10^9$ spores/ml. The mite control composition of the invention may further comprise other active or non-active agriculturally acceptable materials. These may be other miticides and/or agriculturally acceptable carriers, diluents, adjuvants and excipients.

The fungi and compositions of the present invention, and their products may be used for the treatment and prevention of mite infestation in plants that include, but are not limited to, all varieties of citrus plants, apples, grapes, cucumbers, squash and any other commercial plants that are attacked by phytophagous mites.

In Example 1, *M. geulakonigae* is successfully used in the treatment of powdery mildew-infested cucumber plants. Thus, in another embodiment, the fungi and compositions of the present invention and their products may be used for the control of phytopathogenic fungi. In a preferred embodiment, the invention is for the treatment and/or prevention of cucumber powdery mildew, *Sphaerotheca fusca* infestation, as well as that of other powdery mildews in different crops, and other genera and species of phytopathogenic fungi.

Compositions for the control of fungi comprise an aqueous suspension, containing between about $10^7$ to $10^{10}$ spores/ml, preferably $10^9$ spores/ml. The fungus control compositions of the invention may further comprise other active or non-active agriculturally acceptable materials. These may be other miticides, fungicides, and/or agriculturally acceptable carriers, diluents, adjuvants and excipients.

The fungi and anti-fungal compositions of the invention may be used for the treatment of various crops. Such crops may be, but are not limited to, cucumber, tomato, eggplant, pepper, apple, grapes and all commercial crops susceptible to phytopathogenic fungi.

In a further aspect, the invention comprises a method for the production or preparation of a fungicide and/or a miticide, wherein the active ingredient of said fungicide/miticide is any one of *M. geulakonigae*, *M. argovae*, or *A. ingoldii*, or any combination thereof, and/or a culture thereof, and/or any product or derivative thereof. This process comprises culturing a fungus of the invention, and optionally isolating said active ingredient from the culture.

In a particular embodiment, the method comprises the steps of: (a) cultivating, under aerobic or anaerobic conditions, any one of the fungi of the invention in an appropriate culture medium; (b) harvesting the culture; (c) separating the spores from the liquid medium; and either (d) suspending the spores in an agriculturally compatible liquid carrier to give a fungicide/miticide in liquid form; or (e) lyophilizing the spores, to give a dry form fungicide/miticide. Said dry form fungicide/miticide can be further dissolved in an agriculturally compatible liquid carrier. Optionally, the spores may be washed with deionized water after they are separated from the liquid medium.

In the above-described method, the fungus is to be cultured at a temperature of from about 20° C. to about 30° C., preferably from about 23° C. to about 27° C., and more preferably at about 25° C. The pH of the fungi culture should be from about 5.1 to about 5.6, preferably a pH of 5.1 is ideal.

In one embodiment, the fungicide/miticide is an aqueous suspension of spores, obtained through cultivating, under aerobic or anaerobic conditions, any one of the fungi *M. geulakonigae, M. argovae* or *A. ingoldii* (all nom. prov.) in an appropriate culture medium.

In a second embodiment, the fungicide/miticide of the invention is a lyophilized of fungus spores, obtained through the above-described method, wherein the spores are from any one of the fungi *M. geulakonigae, M. argovae* or *A. ingoldii*. This lyophilized form may be advantageous for storage and handling of the fungicide/miticide.

The composition may be prepared in any known manner, e.g. by supplementing the active ingredient with agriculturally acceptable carriers, auxiliaries or diluents, such as solvents, emulsifiers and dispersants or surfactants.

Solvents suitable for use in the invention and its various products include, but are not limited to, aromatics, e.g. xylene; chlorinated aromatics, e.g. chlorobenzenes; paraffins, e.g. mineral oil fractions; alcohols, e.g. methanol and butanol; ketones, e.g. cyclohexanone; amines, e.g. ethanolamine and dimethylformamide; and water, preferably deionized. When water is used, other organic solvents may also be used as co-solvents.

Carriers suitable for use in the invention and its products include, but are not limited to, ground natural or synthetic minerals, e.g. kaolins, clays, talc, chalk, silica, silicates, and the like.

Emulsifiers suitable for use in the compositions of the invention include, but are not limited to, nonionic and anionic emulsifiers, e.g. polyoxyethylene fatty alcohol ethers, alkylsulfonates, arylsulfonates, and the like.

Dispersants suitable for use in the compositions of the invention include, but are not limited to, lignosulfite waste liquors and methylcellulose; and the like.

Suitable surfactants include, but are not limited to, lignophenol-, naphthalene- and dibutylnaphthalenesulfonic acid, fatty acids, alkyl- and alkylarylsulfonates, alkyl lauryl ether and fatty alcohol sulfates, salts of sulfated hexa-, hepta- and octadecanols and of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated iso-octyl-, octyl- or nonylphenol, alkylphenol polyglycol ethers, tributylphenyl polyglycol ether, alkyllauryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

In yet another aspect the invention comprises the use of the novel species and their products in a method for the control and/or prevention of mites (Acari) and/or fungi infestation in plants.

In one embodiment, the method comprises spraying the plant, before or after an infestation by Acari or an infection by fungi, with a composition comprising a suspension of spores of any one of the fungi *M. geulakonigae, M. argovae* or *A. ingoldii* (all nom. prov.), or a mixture of at least two thereof.

The plants grow very rapidly, and fungal infections and acarine infestations happen repeatedly, also due to their windborne nature. Thus, preferably, in the above-mentioned method, the composition is to be applied on the plant weekly or bi-weekly, during the season. This procedure is similar to that used with chemical pesticides.

For the purpose of application, the miticide or fungicide suspension can be used directly or formulated as compositions suitable for spraying, atomizing, dusting, spreading or pouring. For instance, the compositions can be formulated as ready-to-spray solutions, powders, suspensions, highly concentrated aqueous, oily or other suspensions or dispersions, emulsions, oil dispersions, pastes, dusts, or granules.

The non-toxic aqueous pesticide may also contain various additives such as antioxidants, preservatives, pH neutralizers and/or clarifiers.

In use, the non-toxic aqueous pesticide is diluted and sprayed or misted on the infested host, whether plant or animal, to directly contact the surface of the target pests. In some cases, repeated applications may be required.

To enhance the efficiency of the application, the fungicidal/acaricidal composition of the invention may also comprise other active ingredients, such as herbicides, insecticides, growth stimulators, fertilizers and the like.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Source of the Fungi:

Two of the fungal species, namely *M. geulakonigae* and *A. ingoldii* (all nom. prov.), were obtained from cadavers of the citrus rust mite in different sites in Israel, from the Upper Galilee to the south of the Coastal Plain. The third species, *M. argovae* (nom. prov.), was isolated from the carmine spider mite found on a leaf of castor bean at the central Coastal Plain.

Large-Scale Production of Fungi:

All three fungi were mass-cultured in the laboratory on the common solid medium, PDA (potato dextrose agar, Difco) and on the liquid medium PB (potato broth, Difco), at the optimal temperature of 25° C. The fungi have a very rapid life cycle, and maximal production of spores took place within 4 to 5 days. Thus, very large amounts of spores were obtained within a short period of time.

Preparation of the Suspension:

Spores were washed off from the culture grown on PDA with deionized water and their amount (per ml) adjusted to the required concentration with a haemocytometer. The spores were separated from the liquid medium by centrifugation. Deionized water was added and their concentration was adjusted as above.

Application of the Fungicide:

Experiments with powdery mildew (PM) were conducted in the laboratory and in the greenhouse, and one experiment was conducted in a pilot commercial greenhouse. Suspensions of *M. geulakonigae* ($2 \times 10^8$ spores/ml) were sprayed onto cucumber leaves. Leaf coverage by PM and number of leaves killed by the disease were assayed, and the dry matter of the entire plants, and their yields, were weighed.

Application of the Acaricide:

Plants were sprayed as described above, with a suspension of *M. geulakonigae* of about $10^9$ spores/ml.

Example 1

Initial experiments were undertaken to assay the effect of the three new fungi species *M. geulakonigae, M. argovae* and *A. ingoldii* (all nom. prov.) on cucumber powdery mildew infecting detached leaves. Treated leaves were sprayed with each one of the fungi, while control leaves were not sprayed, and then all the leaves were inoculated with powdery mildew. Disease was assessed as the leaf area covered by the powdery mildew, and the experiment was followed weekly for a period of four weeks. At the end of four weeks, the results obtained were as follows. Control leaves had between 50 to 100% of their area covered by the fungi within the first week, which was then followed by leaf mortality. In contrast, the leaves treated with either *M. geulakonigae, M. argovae* or *A. ingoldii* (all nom. prov.) usually had less than 10% of their area covered by the powdery mildew after 15 days. The infection covered area then increased to about 25% at the end of four weeks, by which time most leaves were still alive.

Figure 3:
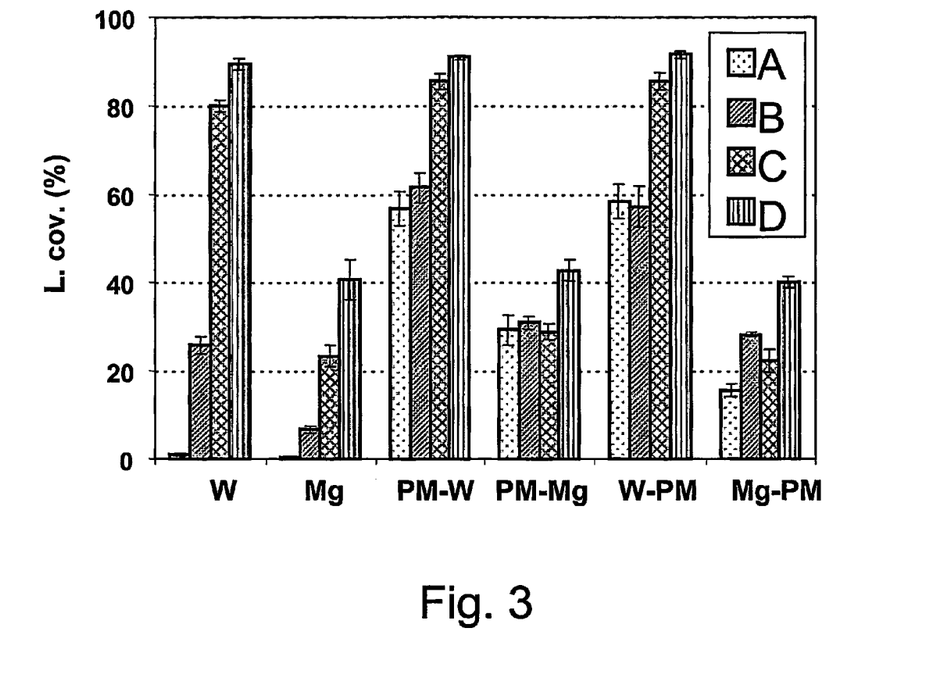
FIG. 3: Effect of treatment by *Meira geulakonigae* nom. prov. (*M. geulakonigae*) on the extent of damage caused by powdery mildew (*Sphaerotheca fusca*) to infected cucumber plants.

After the successful results obtained in the initial experiments with all three fungi, a more systematic study was performed using only *M. geulakonigae* for the treatment of powdery mildew infection on cucumbers. Thus, cucumber plants were sprayed with a *M. geulakonigae* (Mg) suspension, before or after infection by powdery mildew (PM). Various treatment protocols were used: no infection and only water treatment (W in FIG. 3); no infection and only *M. geulakonigae* treatment (Mg in FIG. 3); PM infection first, and then water treatment (PM-W in FIG. 3); infection first, and then *M. geulakonigae* treatment (PM-Mg in FIG. 3); water treatment first, and then infection with PM (W-PM in FIG. 3); *M. geulakonigae* treatment first, then PM infection (Mg-PM in FIG. 3). The following parameters were analyzed:

(a) The extent (percentage) of PM coverage on cucumber leaves was evaluated according to the method of Horsfall & Barratt [Horsfall, J. G. & Barratt, R. W. *Phytopathology.* 35: 655 (1945)] 13, 20, 27 and 53 days post-treatment, and compared to control plants treated with water. PM coverage was faster in the absence of *M. geulakonigae* treatment (FIG. 1, W, PM-W and W-PM) than in its presence (Mg, PM-Mg and Mg-PM), showing the significant bio-control effect of *M. geulakonigae* on the pathogenic fungus.

Figure 4:
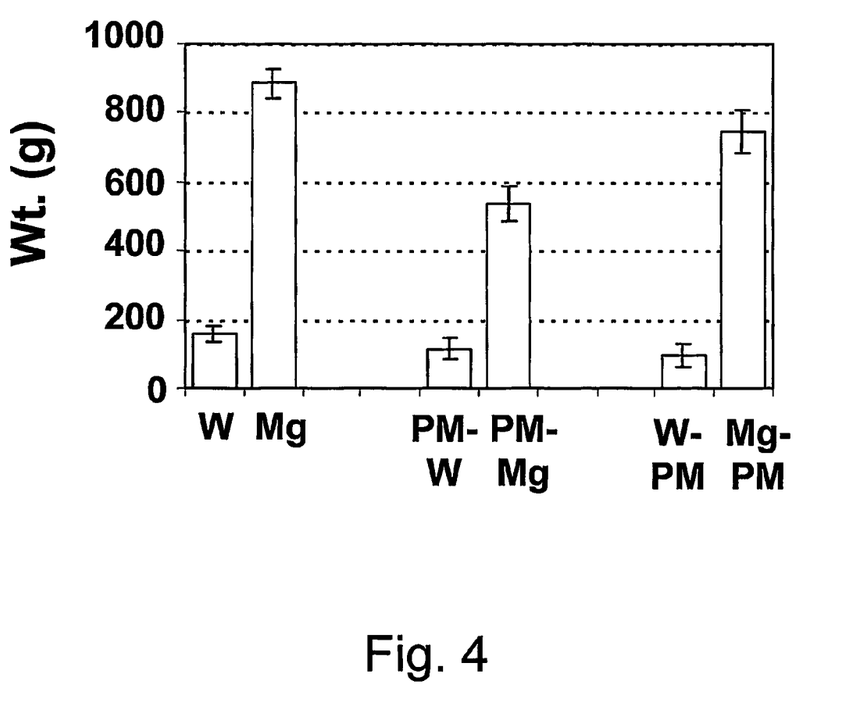
FIG. 4: *Meira geulakonigae* nom. prov. increases the yield of cucumber plants infected by powdery mildew (*Sphaerotheca fusca*).

(b) The yield of cucumbers (in grams, g) from plants sprayed with *M. geulakonigae* was consistently and significantly higher than the yield of cucumbers from untreated plants (FIG. 4).

Figure 5A:
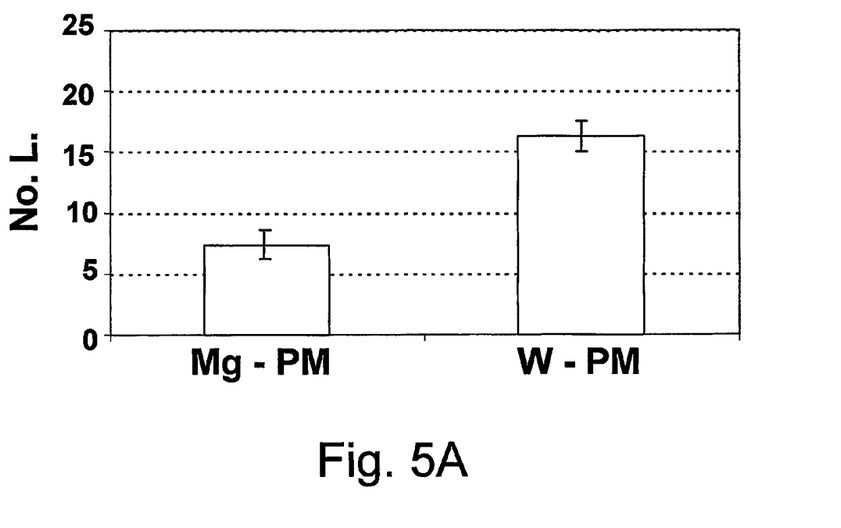
FIG. 5A: Graph showing the effect of *M. geulakonigae* on (A) number of cucumber leaves killed by powdery mildew (*Sphaerotheca fusca*).

(c) The number of dead leaves on cucumber plants sprayed with a suspension of Mg was significantly lower than on plants infected by PM but not given the Mg treatment (FIG. 5A).

Figure 5B:
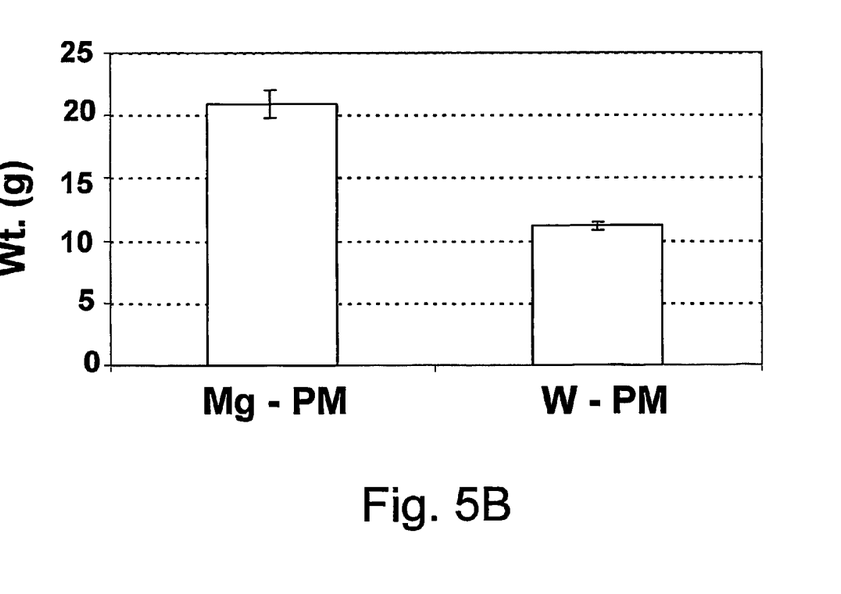
FIG. 5B: Graph showing the effect of *M. geulakonigae* on cucumber yield. Different treatments are represented by the abbreviations as in FIG. 3. Abbreviations: No. L., number of leaves; Wt., weight.

(d) The dry weight of *M. geulakonigae* treated plants was significantly higher than the dry weight of untreated plants (FIG. 5B).

Figure 6A:
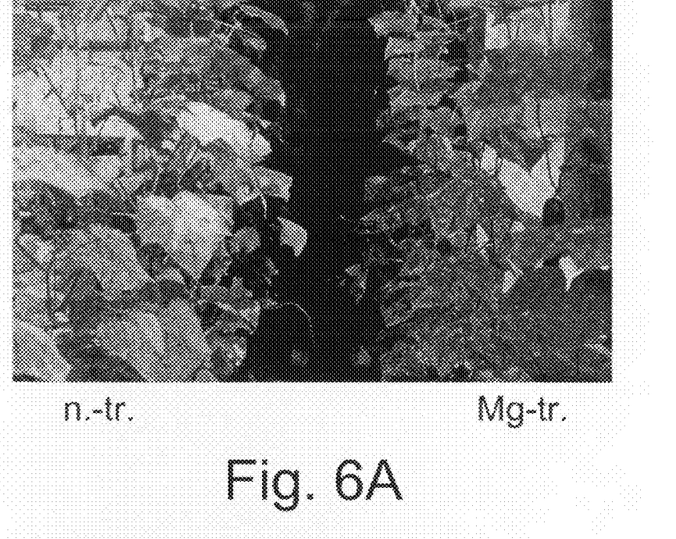
FIG. 6A: General view of the effect of *M. geulakonigae* treatment on cucumber plants infected by powdery mildew (PM) in a pilot commercial greenhouse. Right: natural infection of PM on cucumber plants that were treated with *M. geulakonigae*. Left: natural infection of PM on cucumber plants.
Figure 6B:
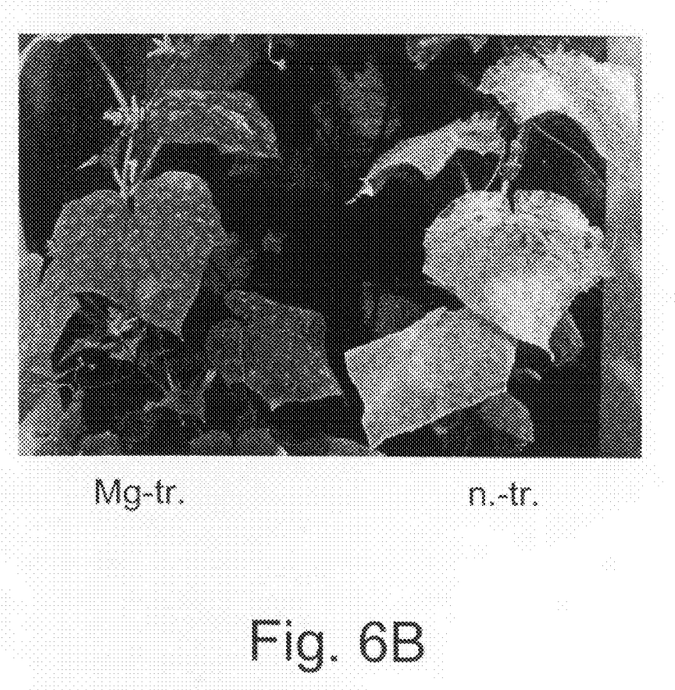

Clear evidence of the bio-control effect of *M. geulakonigae* on powdery mildew infecting cucumbers can be appreciated in the photographs presented in FIG. 6.

Example 2

Figure 7:
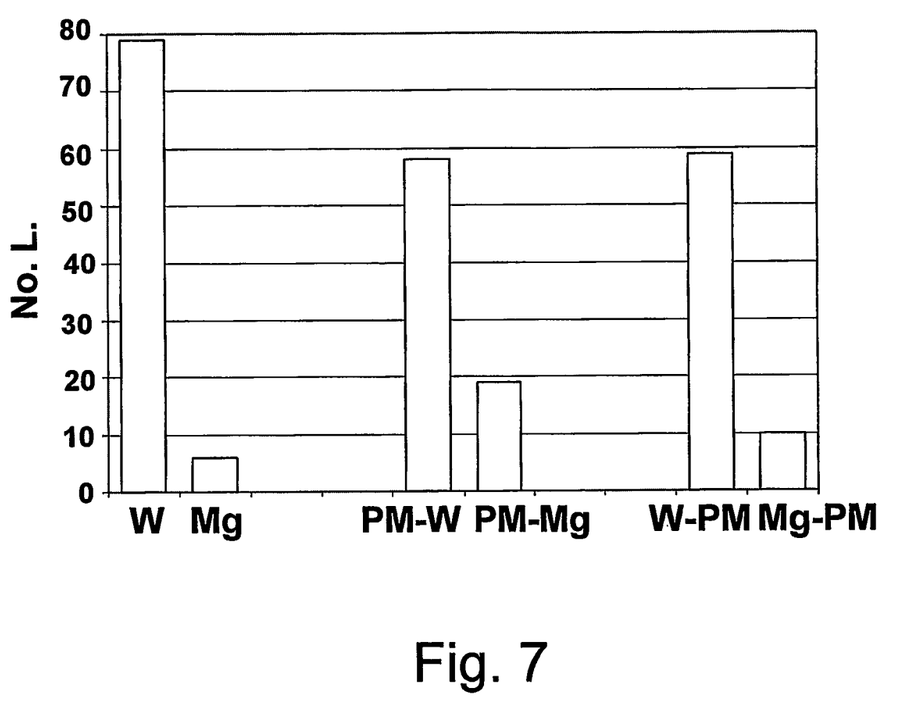
FIG. 7: *Meira geulakonigae* nom. prov. reduces carmine spider mite (*Tetranychus cinnabarinus*) infestation on cucumber plants.

The effect of *M. geulakonigae* treatment on the plant-feeding carmine spider mite (*Tetranychus cinnabarinus*) infesting cucumbers was tested. This mite is a major pest of many crops. The plants were treated using the same protocol as described in Example 1. In order to avoid destructive sampling, the number of leaves infested by at least one live adult spider mite was counted. The data was obtained from 5 leaves per plant and 6 plants per treatment. Thus, a total of 30 leaves were evaluated on each observation date. All leaves that were not treated with *M. geulakonigae* had significantly larger spider mite populations (FIG. 7) and at times showed heavy mite damage.

Example 3

One initial experiment was conducted with the major citrus pest, the citrus rust mite *Phyllocoptruta oleivora* as target, using all three new fungi for pest control. Table 1 shows the results obtained for this initial experiment, the numbers represent the percentage of mites killed after treatment, calculated with Abbott's correction. The names of all three fungi are provisional.

TABLE 1

| Control | A. ingoldii | M. geulakonigae | M. argovae |
|---------|-------------|-----------------|------------|
| 15.2    | 96.5        | 95.3            | 92.3       |

Figure 8:
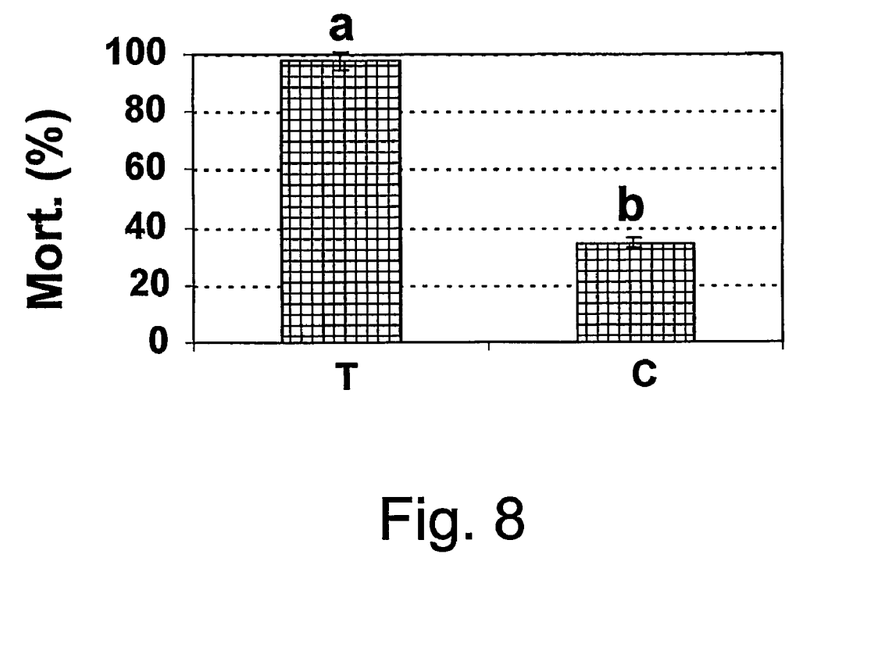
FIG. 8: *Meira geulakonigae* nom. prov. increases the mortality of citrus rust mite (*Phyllocoptruta oleivora*) on citrus leaves.

Following the results of the initial experiment using the three new fungi species, a second experiment was conducted on the effect of *M. geulakonigae* on the citrus rust mite. Heavily-infested citrus seedlings were sprayed with *M. geulakonigae* suspensions of $10^9$ spores/ml, obtained after liquid fermentation of the fungus. Pest mortality was almost 100% (after Abbott's correction) in the treated plants, as compared to about 30% in the untreated control (FIG. 8).

The invention claimed is:

1. A biocontrol composition for the control of mites and/or phytopathogenic fungi wherein said composition comprises spores and/or conidia from a biologically pure culture of a fungus selected from the group consisting of *Meira geulakonigae* Accession No. CBS 109902, *Meira argovae* Accession No. CBS 109903, and *Acaromyces ingoldii* Accession No. CBS 109901.

2. The composition of claim 1, further comprising an agriculturally compatible carrier.

3. The composition of claim 2, wherein said carrier is an extract of a liquid culture medium in which said fungus has been cultured.

4. The composition of claim 2, wherein said carrier is water a culture medium, or an oil.

5. The composition of claim 3, wherein said composition is in the form of a liquid suspension containing about $10^7$ to about $10^{10}$ spores/ml of said fungus.

6. The composition of claim 5, wherein the suspension contains about $10^9$ spores/ml.

7. The composition of claim 1, further comprising an adjuvant.

8. A method of controlling mite infestation in a plant susceptible thereto, said method comprising the step of applying to said plant a composition for the control of mites as defined in claim 1.

9. The method of claim 8, wherein the mite infestation is caused by *Phyllocoptruta oleivora* (citrus rust mite), *Tetranychus cinnabarinus* (carmine spider mite), and/or *Panonychus citri* (cirrus red mite).

10. The method of claim 9, wherein said plant is any commercial plant susceptible to spider mites, rust mites, gall mites or phytopathogenic fungal diseases.

* * * * *